United States Patent [19]

Davis et al.

[11] Patent Number: 4,817,629
[45] Date of Patent: Apr. 4, 1989

[54] PROCESS AND APPARATUS FOR MEASUREMENT AND MONITORING OF MUSCLE COMPARTMENT PRESSURE

[75] Inventors: Scott J. Davis, Kalamazoo; Wayne N. Warfield, Schoolcraft Township, Kalamazoo County; William M. Booth, III, Paw Paw Township, Van Buren County, all of Mich.

[73] Assignee: Stryker Corporation, Kalamazoo, Mich.

[21] Appl. No.: 15,835

[22] Filed: Feb. 18, 1987

Related U.S. Application Data

[63] Continuation-in-part of Ser. No. 815,848, Jan. 3, 1986, abandoned.

[51] Int. Cl.$^4$ .............................................. A61B 5/00
[52] U.S. Cl. ................................... 128/748; 128/675; 604/160
[58] Field of Search ............... 128/672.3, 675, 748; 604/236–237, 160

[56] References Cited

U.S. PATENT DOCUMENTS

| | | | |
|---|---|---|---|
| Re. 30,966 | 6/1982 | Hargens et al. | 128/673 X |
| 2,535,998 | 12/1950 | Bierman | 128/675 X |
| 2,600,324 | 6/1952 | Rappaport | 128/675 X |
| 2,866,453 | 12/1958 | Jewett | 128/748 X |
| 3,601,151 | 8/1971 | Winnard | 604/236 X |
| 3,651,807 | 3/1972 | Huggins | 604/161 |
| 3,720,201 | 3/1973 | Ramsey, III | 128/748 |
| 3,880,151 | 4/1975 | Nilsson et al. | 128/673 |
| 4,114,603 | 9/1978 | Wilkinson | 128/748 |
| 4,136,681 | 1/1979 | Hon | 128/748 |
| 4,160,448 | 7/1979 | Jackson | 128/673 |
| 4,185,641 | 1/1980 | Minior et al. | 128/675 |
| 4,192,319 | 3/1980 | Hargens et al. | 128/673 |
| 4,209,023 | 6/1980 | Layton | 128/748 |
| 4,215,699 | 8/1980 | Patel | 128/748 |
| 4,341,224 | 7/1982 | Stevens | 128/673 X |
| 4,377,165 | 3/1983 | Luther et al. | 604/160 |
| 4,398,542 | 8/1983 | Cunningham et al. | 128/748 X |
| 4,423,740 | 1/1984 | Castle et al. | 128/748 |
| 4,449,973 | 5/1984 | Luther | 604/161 |

Primary Examiner—Kyle L. Howell
Assistant Examiner—Angela D. Sykes
Attorney, Agent, or Firm—Flynn, Thiel, Boutell & Tanis

[57] ABSTRACT

Portable apparatus for measuring and monitoring muscle compartment pressures comprising a system of a disposable assembly of a syringe, a pressure chamber having a diaphragm, and means to penetrate the skin of a patient, and a measuring and reading device comprising a transducer, whereby accurate measurement of such pressures can be easily made.

14 Claims, 2 Drawing Sheets

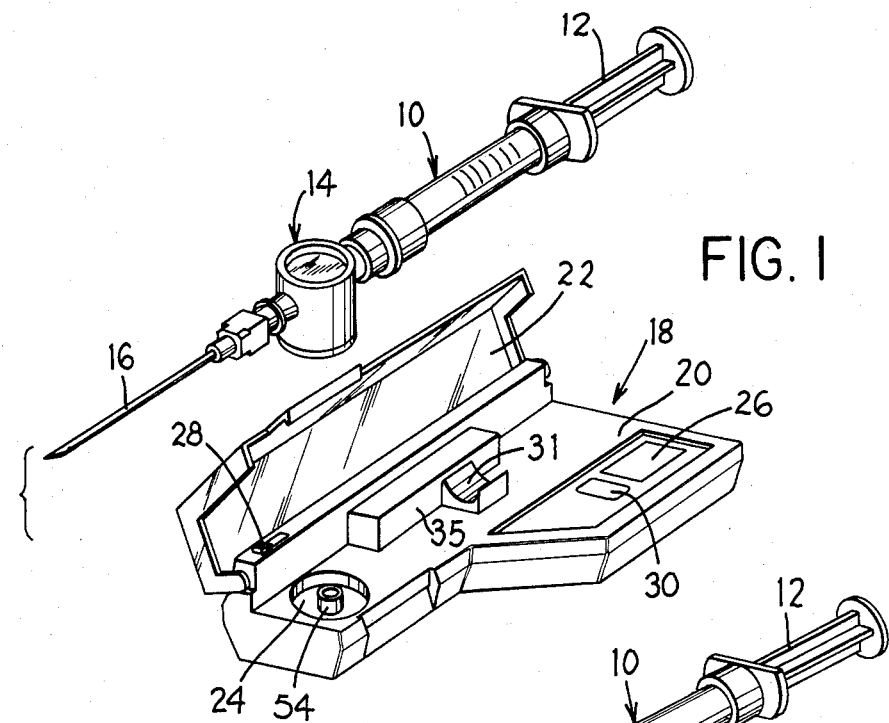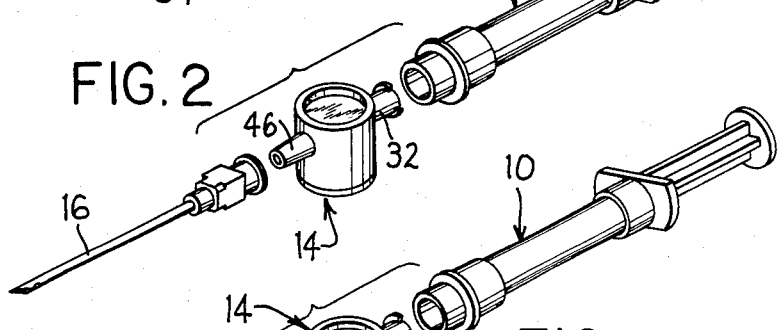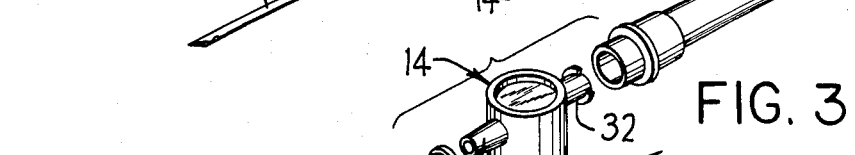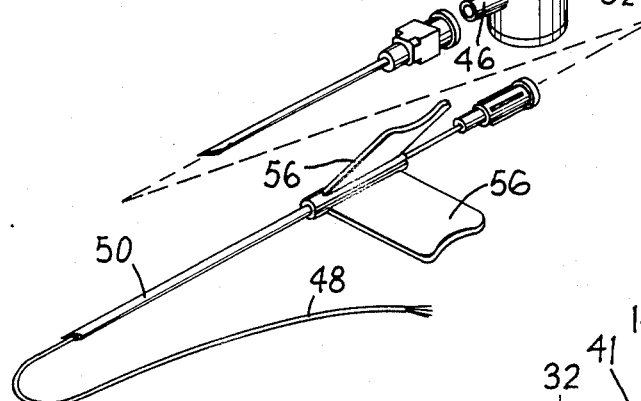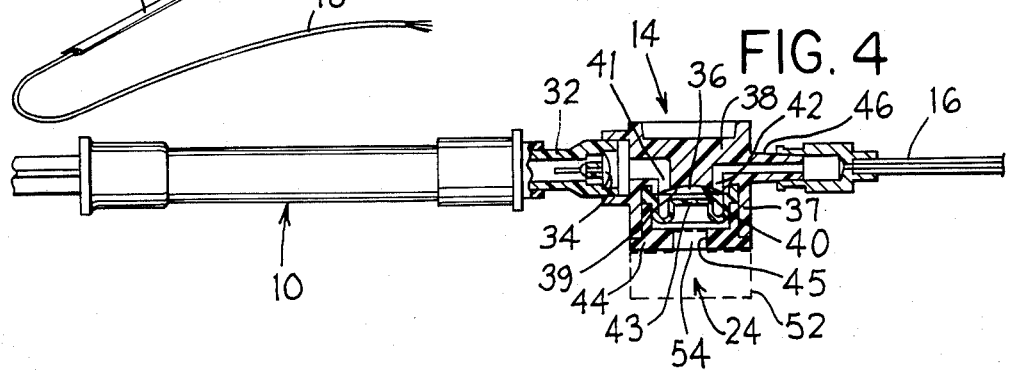

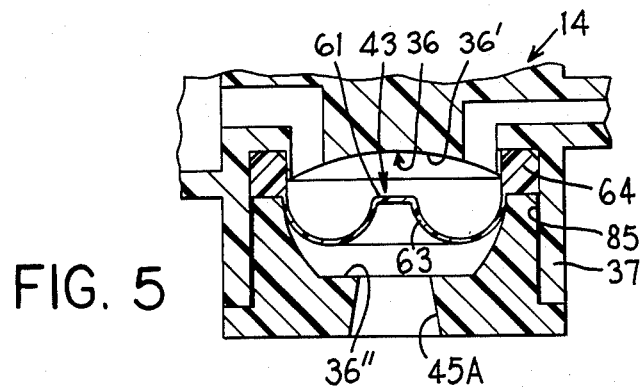
FIG. 5
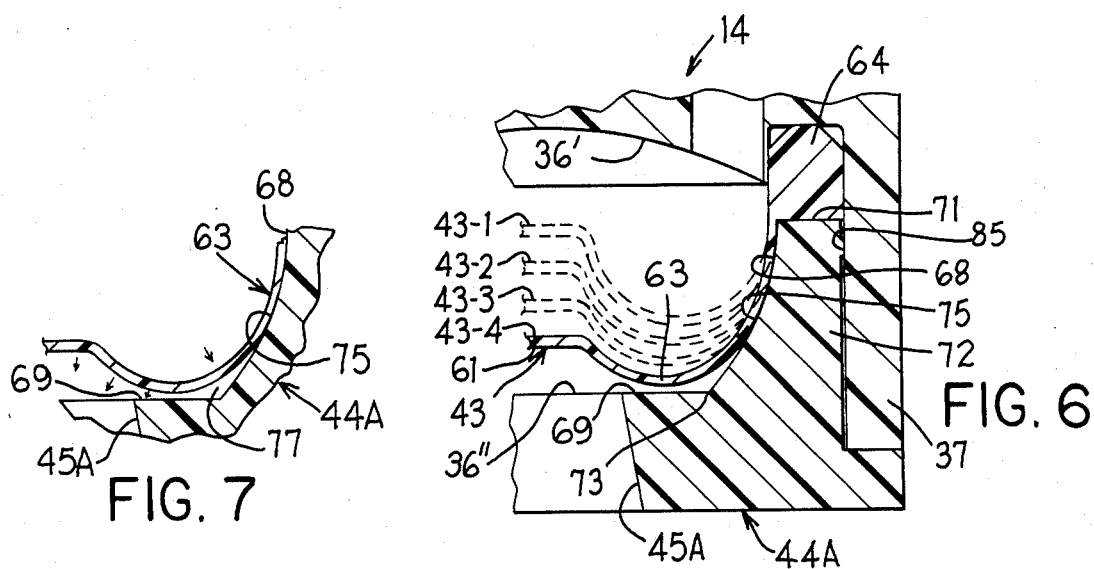
FIG. 7
FIG. 6
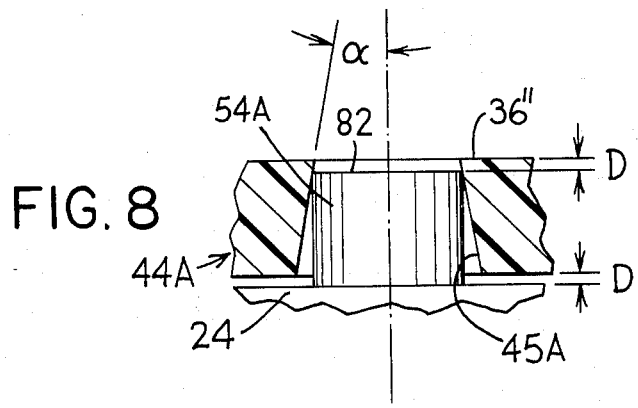
FIG. 8

PROCESS AND APPARATUS FOR MEASUREMENT AND MONITORING OF MUSCLE COMPARTMENT PRESSURE

This application is a continuation-in-part of our prior application Ser. No. 815,848 filed Jan. 3, 1986 and now abandoned.

BACKGROUND OF THE INVENTION

1. Field of the Invention

This invention relates to process and apparatus for measuring and monitoring muscle compartment pressure or interstitial tissue pressure.

Interstitial tissue pressure measuring and monitoring is useful for diagnosis and amelioration of the effects of acute compartment syndromes. Trauma can cause the pressure in tissue confined within a body compartment to increase to a level which is uncomfortable or causes muscle and nerve damage. It is desired to diagnose this pressure build-up as soon as possible so that corrective procedures can be performed to remove the excess fluid, thereby reducing the harmful pressure and preventing permanent damage.

2. Discussion of Prior Art

U.S. Pat. No. 4,423,740, granted Jan. 3, 1984 to Castle et al, discloses "An interstitial tissue measuring device comprising a cannula and a catheter, the catheter being adapted to pass through the cannula and the distal end of the catheter being provided with a plurality of longitudinal slits defining a plurality of petals between them. When the cannula is emplaced in an interstitial tissue site and the catheter is passed through the emplaced cannula into the tissue, the petals facilitate measurement of pressure by a pressure-sensing device at the proximal end of the catheter". The pressure sensing device is only identified as such and is not described in any manner. The claims of the patent are directed to the method of using the described device.

U.S. Pat. No. 4,185,641, granted Jan. 29, 1980 to Minior et al, relates to a pressure dome which is provided with resilient tongues that engage projections on a transducer, so as to draw the dome and transducer together. A given contact pressure is applied between the flexible membrane of the pressure dome and the diaphragm of the transducer. The apparatus described is useful in monitoring the blood pressure of a patient.

U.S. Pat. No. 2,866,453, granted Dec. 30, 1958 to Jewett, relates to a direct reading hypodermic pressure indicating device. The device comprises a syringe, a hypodermic needle, a manometer, a stopcock, and a fluid chamber having a flexible diaphragm thereacross. The needle and the syringe are connected to opposite ends of the stopcock; the manometer contains an indicating fluid and is connected to the fluid chamber which is also connected to the stopcock. By turning the handle of the stopcock, blood is directed into the fluid chamber to exert pressure on the diaphragm. The pressure is transmitted by the diaphragm to the indicating fluid in the manometer whose scale can be visually read.

U.S. Pat. No. 2,600,324, granted June 10, 1952 to Rappaport, discloses electrical circuitry for use with a transducer in a fluid pressure measuring system.

SUMMARY OF THE INVENTION

The invention to be described herein relates to an improved, portable and partly disposable compartment syndrome pressure reading and monitoring system and process of using same. The system comprises a disposable assembly of a syringe, a pressure chamber having a flexible diaphragm, and means to penetrate the skin of a patient. A one-way valve is located between the syringe and the pressure chamber, and the pressure chamber has an opening defined by a surrounding wall of a determined height. The opening, generally circular, is covered by the diaphragm whose height is less than that of the surrounding wall.

The remainder of the system, the monitoring and pressure reading device, comprises a transducer, such as a strain gage type device for measuring pressure, and means to translate signals of the transducer into a form which can be visually read by an attending physician or trained nurse.

The complete system is portable and self-contained without external electrical wiring and/or connections. It is simple in construction, accurate, and easy to use, so that compartmental pressure measurements can be made on a routine basis.

BRIEF DESCRIPTION OF THE DRAWING

FIG. 1 is an isometric illustration of the pressure measuring and monitoring system of this invention;

FIG. 2 is an isometric illustration of one form of the disposable assembly used in the system of this invention;

FIG. 3 is an isometric illustration of another form of the disposable assembly used in the system of this invention; and FIG. 4 is a partial sectional view of the disposable assembly of the form shown in FIG. 2, showing in section the pressure chamber, its opening and defining wall, the diaphragm, and the one-way valve, and also in broken lines, the position of the diaphragm relative to the transducer of the system.

FIG. 5 is an enlarged fragment of FIG. 4 showing a modification of a cap closing the bottom of the pressure chamber and with the diaphragm in its rest (no pressure drop thereacross) position.

FIG. 6 is an enlarged fragment of FIG. 5 showing the diaphragm in solid line in its upper nonpressurized, rest condition and showing in broken lines intermediate positions between such rest position and a lower pressurized position of the diaphragm.

FIG. 7 is a fragment of FIG. 6.

FIG. 8 is an enlarged fragment of FIG. 5 showing an improved sealing arrangement between the projection of the transducer and the central opening in the bottom of the cap.

DETAILED DESCRIPTION OF THE PREFERRED EMBODIMENTS

Looking at the drawing, FIG. 1 illustrates a portable assembly of a syringe 10 having a plunger 12, a pressure chamber housing 14, a needle 16, and a pressure sensing and reading device or monitoring device 18. The device 18 comprises a housing 20 with a transparent hinged lid 22 enclosing a pressure responsive transducer 24, a direct reading dial or display 26 calibrated preferably in millimeters of mercury or inches of water, as is customary for reading pressures of the nature contemplated. The reading can be in analog or digital form. The housing also encloses the necessary electrical circuitry (not shown), an on-off switch 28 and a zero button 30, the latter to zero the system for use, as will be later explained. The electrical circuitry is a low voltage system and is battery powered, posing no threat to the safety of the patient whose pressure is being taken. The batteries are housed in a battery box 35 in the housing 20. Electrical circuitry for converting transducer-measured fluid pressures to visual readouts is well known in the art and needs no further explanation. The housing 20 has a cradle 31 for supporting the syringe 10.

The syringe 10 is connected by a press-fit onto a nipple-like projection 32 of the pressure chamber 14. Referring to FIG. 4, the pressure chamber 14 incorporates a one-way valve 34 which permits fluid to pass from the syringe 10 into the pressure chamber housing 14, but prevents the back-flow of fluid into the syringe from the pressure chamber housing. The one-way valve 34 is of conventional construction and needs no further explanation. The pressure chamber housing 14 is provided with a generally circular internal chamber 36 defined by a circular side wall 37 and a top wall 38. The top wall 38 has a central projection 39 extending downwardly therefrom. The bottom surface 40 of the projection 39 is arcuate in cross-section. First and second passages 41 and 42 extend through the top wall 38 and communicate with the chamber 36. A generally circular, resiliently flexible, pressure sensitive, corrugated diaphragm 43 is located in the chamber 36. The perimeter of the diaphragm 43 is received in an annular groove defined by the side wall 37 and the top wall 38 of the housing 14 and is sealed therein by an upstanding wall of a cap 44. The diaphragm 43 divides the chamber 36 into upper and lower sections. The upper section is fluid tight except for the passages 41 and 42 so that the diaphragm 43 is flexed when the pressure changes in passage 42. The cap 44 has a central opening 45 which receives the projection 54 from the transducer 24 so that the lower side of the chamber 36 is sealed by said projection.

The pressure chamber housing 14 is also provided with a nipple-like projection 46 opposite the projection 32. The needle 16 (FIG. 2) or a unit comprising catheter 48 surrounded by a cannula 50 (FIG. 3) is press fit thereon. The disposables, i.e., the syringe 10, the pressure chamber housing 14 and the needle 16 and/or the catheter 48 and cannula 50 are constructed of materials which can be easily sterilized.

The catheter 48 can be of any suitable construction, such as a slit catheter as disclosed in U.S. Pat. No. 4,423,740 or a wick catheter as disclosed in U.S. Pat. No. 4,192,319. The cannula 50 is a pre-split or breakaway cannula needle in which the barrel of the cannula has opposed slits or zones of weakness extending lengthwise therealong. Manually engageable grips 56 are affixed to the wall portions of the cannula between the slits. When the grips 56 are pulled apart, the cannula splits in half along the length thereof whereby the cannula is separated from the cannula. For further details about breakaway cannulas of this type, reference is made to U.S. Pat. Nos. 4,377,165 and 4,449,973.

The pressure sensing and reading or monitoring device 18, illustrated in FIG. 1 and partly in broken lines in FIG. 4, as previously stated, incorporates the transducer 24 which has a generally circular housing 52 and a hollow cylindrical projection 54 that extends into the opening 45 in cap 44. When assembled as shown in FIG. 4, air is trapped between the diaphragm 43 and the transducer 24 with the diaphragm 43 being disposed generally parallel with the pressure responsive element of the transducer. Movement of the diaphragm 43 in response to pressure in the upper section of compartment 36 is transmitted to the transducer 24 through the trapped air. This arrangement has been found to provide more stable readings than if the diaphragm 43 physically contacted the transducer 24.

When a "quick" pressure reading or several pressure readings at different locations in the compartment are desired, the needle assembly 16 is used; when monitoring pressures in a compartment over an extended period of time is desired, a catheter and cannula assembly is used.

OPERATION

To use the system described using the needle 16, the assembled disposables (syringe 10 filled with a sterile saline solution, pressure chamber housing 14 with diaphragm 43, and needle 16) are assembled using a sterile technique, placed in the monitoring device 18 with the diaphragm 43 facing the transducer 24 as shown in FIG. 4, and the cover 22 is closed. This assembly is held vertically, needle up, and the plunger 12 is depressed to purge the system of air.

The site (skin of the patient) above the compartment to be measured is cleaned using standard surgical skin prep techniques.

The complete disposable and monitoring system is positioned above the skin at the point of entry at an angle approximating the final angle of the system after introduction of the needle into the compartment or tissues. A small droplet of saline solution is raised on the needle point, the zero button on the monitor is pressed to zero out the system and eliminate any pressure differential due to the difference in height of the needle point and transducer. The needle 16 is then introduced into the body compartment and approximately 0.2 cc of saline solution is injected into the compartment to form a pressure transmitting pocket at the tip of the needle. The pressure in the body compartment can then be read on the read out device 26. After the pressure is read, the needle 16 is withdrawn. Subsequent measurements in the same or other compartments of the same patient can be made with the same needle using the same procedure.

The procedure for using the catheter 48 and cannula 50 is similar to that used to introduce a flexible catheter for IV introduction. The catheter 48 is disposed inside the cannula 50 so that the end of the catheter is close to, but is slightly spaced from the tip of the cannula. The assembly of the catheter and cannula is attached to the pressure chamber housing 14 and then the syringe 10 is placed on the monitor 18 and is purged of air. The relationship of the monitor and the tip of the cannula are determined, a drop of saline solution is raised on the tip of the cannula, the monitor is zeroed with the positions of the tip of the catheter 48 and the monitoring device 18 being approximately in their final positions, and then the cannula containing the catheter therein is penetrated into the body compartment. The cannula is then withdrawn by sliding it lengthwise back over the catheter, leaving the catheter in place inside the body compartment. The catheter is taped in place and then the cannula is split-apart to remove it from the catheter. Approximately 0.2 cc of saline solution is introduced into the compartment. The pressure is read on the display 26.

The monitor itself, while not intended for routine sterilization, can be sterilized when and if it becomes heavily contaminated. The disposables are designed to be sterilized by ethylene oxide.

The device is simple, inexpensive and capable of routine use, for example, in an emergency room. Air is used to transfer the pressure in passage 42 to the transducer 24 and this has been found to provide more stable readings. The use of a disposable chamber housing 14 containing the diaphragm, as well as the disposable syringe and needle or cannula-catheter unit is a significant advantage over the use of reusable units. The use of the one-way check valve 34 is a significant simplification in comparison with the use of manually operated stopcocks. The incorporation of the transducer and the read out device into a single portable unit is highly advantageous because the readings are provided in close proximity to the injection site and no remote hardware is required. The transducer 24 functions essentially as a pressure measuring strain gage.

MODIFICATION

In the following discussion, parts corresponding generally to but modified from parts above discussed with respect to FIGS. 1-4 will carry the same reference numerals with the suffix "A" added thereto.

For best accuracy and repeatability of pressure measurement, it is desirable that the diaphragm 43 flex easily from its rest position shown in FIG. 5 to its flexed downward position shown in FIG. 6, so as to transmit substantially all of the pressure in the upper part 36' of the chamber 36 to the central opening 45A. Restated, it is desirable that an absolute minimum of downward force be required to push the central head 61 of the diaphragm from its upper rest position FIG. 5, to its fully lowered position of FIG. 6. The purpose is to minimize error, contributed by downward displacement of the diaphragm head 61, to the reading by transducer 24 of the liquid pressure in the upper part 36' of the chamber 36.

A number of structural features in the above discussed FIG. 4 first embodiment contribute to minimizing such error. These include providing the diaphragm with the thin, deeply depressed, U-shaped cross section, annular suspension portion radially interposed between the rim 64 and central head 61 of the diaphragm 43, the location of the central head 61 and annular suspension portion 63 with respect to the walls of the chamber 36, and the positive fixing and sealing of the substantially square cross section rim 64 continuously on all of four sides of the substantially square cross-section thereof by the opposed surfaces of the cap 44 and pressure chamber housing 14.

However, Applicants have found it possible to reduce further the already low error of the original FIG. 4 configuration.

More particularly, such a further error reduction has been made possible by the modification of FIGS. 5 and 6 in which the interior side and bottom wall surfaces 68 and 69 of the cap 44A are no longer respectively vertically cylindrical and horizontal to meet at a sharp corner as in the original FIG. 4 structure. Instead, the side and bottom wall surfaces 68 and 69 of FIG. 5 together form a continuous concavely curved, or dished, surface extending from near the top 71 of the side wall 72 of the cap 44A downward and radially inward to a point 73 near to but spaced from the central opening 45A. This curved blending of the interior side and bottom walls 68 and 69 is specifically indicated by the reference character 75. In the embodiment shown, the uppermost fraction of the interior side wall surface 68 and the most central fraction of the interior bottom wall surface 69 are respectively still preferably vertical and horizontal.

The curvature 75 is selected to conform closely to the curvature into which the annular suspension portion 63 would naturally flex (unroll) without stretching as the upper part 36' of the chamber 36 is subjected to an increasing liquid pressure. In the embodiment shown the curvature 75 is substantially circular and this portion of the chamber 36' is substantially hemispherical, except for flattening of the bottomwall near the central opening 45A. As pressure in the upper part 36' of the chamber 36 increases relative to the pressure at the central opening 45A, the head of the diaphragm 43 gradually displaces downward from its top (rest) position (shown in solid line FIG. 5 and in the topmost dotted line curve 43-1 in FIG. 6), thence through intermediate positions (shown in dotted lines at 43-2 and 43-3 in FIG. 6) and finally to its lower position indicated in solid line at 43-4 in FIG. 6. As a result, as the central head 61 of the diaphragm displaces downwardly, the U-cross section suspension portion 63 in effect unrolls (much like a carpet being unrolled across a flat floor) downward in close supported contact with and progressively along the curvature 75, as indicated by the several successive dotted line positions 43-1 through 43-4 in FIG. 6. The curvature at 75 is selected purposely so that the downwardly unrolling annular suspension portion 63 is firmly backed by the curved wall surface 75 which avoids stretching of the annular suspension portion 63 and trapping of air between the annular suspension portion 63 and adjacent surface of the cap 44A. This unrolling action is further illustrated in FIG. 7, in which, at a given moment, parts of the downwardly unrolling annular suspension portion 63 move in the direction of the several small arrows.

As the annular suspension portion 63 unrolls along the curved interior wall surface 75 of the cap 44A, a narrow, angular cross-section, squish area 77 advances downwardly and radially inwardly (leftwardly in FIG. 7) therebetween. This expels the air from between the advancing annular suspension portion 63 and curved interior cap wall 75, to avoid entrapping air therebetween 68 and 69. Entrapped air may tend to counteract a fraction of the fluid pressure atop the diaphragm and thus lead to reading error by the transducer 24 of FIG. 4.

The aforementioned avoiding of stretching of the material of the annular suspension portion 63 eliminates error in the pressure applied through the central opening 45A to the transducer 24, which error would otherwise tend to occur due to work done by pressurized liquid in the upper chamber portion 36' in stretching the diaphragm.

Further, the curved interior side wall 75 supports the unrolling annular suspension portion 63 and thus helps to reinforce it against damage by pressure drops applied thereacross. This allows the annular suspension portion 63 to be made of thinner, more flexible material with reduced danger of rupturing in use.

Error in the reading of the transducer 24 is further reduced because the amount of air in the lower portion 36" of the chamber 36 is minimized to the extent possible while still providing room for the diaphragm to move downward from rest. Thus, the amount of air beneath the diaphragm 43 in its lower position 43-4 is minimized to thereby more accurately convey to the transducer 24 the liquid pressure above the diaphragm 43 over the range of liquid pressures to be measured. An extreme (beyond the normal maximum intended to be accurately measured) pressure in the upper part 36' of the chamber 36 can press the diaphragm suspension portion 63 down virtually flat against the bottom wall 69 (down beyond position 43-4 in FIG. 6, still without significant stretching of the diaphragm material).

FIG. 8 discloses a further modification in which the central opening 45A tapers at an angle α from outside the cap 44A toward the bottom chamber portion 36". The sensing projection 54A of the transducer 24 is here cylindrical, although it is contemplated that projection 54A may be slightly tapered at an angle of perhaps half or less the angle α. The diameter at the upper (inner) end 81 of the central opening 45A is slightly less than the outside diameter at the upper end 82 of the sensing projection 54A. Thus, as the sensing projection 54A enters the central opening 45A air can escape therebetween from the lower part 36' of the chamber 36 (namely from below the diaphagm 43), until the upper end 82 of the projection 54A wedgingly engages the wall of the central opening 45A near the upper end 81 of the latter. Thus, airtight sealing therebetween occurs in the last little bit D of final axial displacement of the projection 54A upward in the central opening 45A. The final displacement D is typically in the range 0.005 inch to 0.010 inch but is indicated in an exaggerated manner, for clarity, in FIG. 8. This minimizes the amount by which the final sealing displacement D of the projection 54A into the central opening 45A may tend to compress the air beneath the diaphragm 43 and hence preload the diaphragm 43. Such preload is here limited to about 2 mm of mercury or less, which is small compared to the range of pressures to be measured.

Note that a possible source of error is avoided in both embodiments by locating the downwardly extending legs of the passages 41 and 42 radially very close to the inner periphery of the rim of the diaphragm 43. Thus, when the apparatus is tipped vertically (needle 16 up) and the syringe is partially actuated to cause liquid therefrom to eliminate air from the passages 41, 42, the upper chamber part 36' and the needle 16, no air will be trapped in the then upper (rightward in FIG. 4) portion of the chamber 36 between the diaphragm 43 and outlet 42.

In one unit according to FIGS. 5-7, the diaphragm was of silicone silastic material of 40 Durometer, with suspension portion 63 thickness in the range 0.007-0.009 inch, and head 61 thickness in the range 0.009-0.012 inch. The rim 64 was chamfered at its upper corners to facilitate its insertion in the annular recess in the housing 14. The curvature at 75 was circular, of radius in the range 0.247-0.257 inch centered on the top center of the cap 44. An annular ridge 85 on the outside of the cap sidewall, protruding about 0.007-0.011 inch, seals against the sidewall 37 of the housing 14.

In testing an apparatus according to FIGS. 5-8 having an effectife measuring range of 0-160 mm of mercury, it was found that the curvature 75 of the cap sidewall and the tapered configuration of the FIG. 8 central opening 45A reduced average error from about 8 mm of mercury to about 2 mm of mercury, as compared to an apparatus according to FIG. 4.

The angle α in FIG. 8 preferably is about 10°.

The appended claims are intended to cover all reasonable equivalents and are to be interpreted as broadly as the prior art will permit.

The embodiments of the invention in which an exclusive property or privilege is claimed are defined as follows:

1. A tissue fluid pressure measuring and monitoring system, comprising a syringe, a pressure chamber member having a bottom, and a tissue penetrating means aligned in series, said syringe and tissue penetrating means having flow passages, said pressure chamber member being a one piece member coaxially aligned between said syringe and tissue penetrating means;

a cap fitted to the bottom of said pressure chamber member, said pressure chamber member and cap cooperating to define an internal chamber having a top wall, said wall and bottom wall, said bottom wall being annular and having a central opening therethrough, L-shaped connecting passages in said top wall respectively connecting said flow passages with said internal chamber, said L-shaped passages having generally aligned but spaced apart legs respectively connected to said flow passages in said syringe and tissue penetrating means, said L-shaped passages further having respective downward extending parallel, spaced apart legs connecting respective aligned legs with said internal chamber at two points spaced from the center of the chamber, the top wall of said chamber being domed in the central portion thereof and having a substantially square cross section annular recess at the perimeter thereof, said pressure chamber member being free of any valve structure in and between said connecting passages and chamber;

a diaphragm of semitoroidal shape and hence of generally W-shaped cross section, said diaphragm separating top and bottom portions of said chamber, said diaphragm having a rim, a raised central head and a deeply depressed annular suspension portion radially interposed between the rim and central head, said rim being of substantially square cross section and substantially thicker than the rest of said diaphragm, said rim being snugly received in said annular recess in said top of said chamber, the radially outer portion of said rim defining a downward facing annular step, said cap having an upstanding annular cylindrical wall snugly telescopingly received in an annular side wall of said member and at its upper edge abutting said annular step of said diaphragm rim, the edge of said domed portion of said top wall of said member lying at an intermediate level in the height of said rim, all four sides of said rim being in sealing engagement with opposed surfaces of said pressure chamber member and cap, said depressed annular suspension portion being of deep U-shaped cross section and extending from said rim down to near the bottom wall of said chamber, said central head having a rest (no pressure differential thereacross) position at about the level of said step of the rim and spaced above the bottom of said annular suspension portion, said downwardly extending legs of said L-shaped connecting passages opening through the top wall of said chamber vertically opposite said depressed annular suspension portion and substantially flush with said rim and the radially outer wall of said annular suspension portion of said diaphragm to prevent trapping air between the diaphragm and chamber top wall when the syringe is activated to drive liquid through said pressure chamber member and tissue penetrating means, the central opening in the bottom wall of said chamber being spaced opposite said raised central head of said diaphragm by more than the depth of said depressed annular suspension portion and said depressed annular suspension portion being radially outboard of said central opening in said bottom wall so that said central opening is free of blocking by said diaphragm;

a pressure transducer positionable at said central opening, whereby movement of said diaphragm caused by pressure in said tissue is detected by said pressure transducer.

2. A tissue pressure measuring and monitoring system as recited in claim 1, wherein said syringe, said pressure chamber member and said tissue penetrating means are separable from said pressure transducer and are disposable after use.

3. A tissue pressure measuring and monitoring system as recited in claim 2, wherein said tissue penetrating means comprises a needle.

4. A tissue pressure measuring and monitoring system as recited in claim 2, wherein said tissue penetrating means comprises a catheter and a cannula.

5. A tissue pressure measuring and monitoring system as recited in claim 1, including a measuring device including a housing having a support surface on which to lay said syringe, said pressure transducer being located on said housing adjacent said support surface and having a projection sealingly receivable in said central opening in said annular bottom wall of said cap with said syringe laid on said support surface of said housing, said housing having a cover closable over said support surface to hold said syringe in place on said support surface and said cap in place on said transducer, said housing having oppositely open holes through which a manually actuable portion of said syringe projects and from which oppositely projects said tissue penetrating means, said housing having pressure read out means outside and adjacent said cover for reading out the pressure in said chamber.

6. A tissue pressure measuring and monitoring system as recited in claim 1 in which the side wall of said chamber is concavely curved downward and then radially inward to meet the bottom wall of said chamber, so that the portion of said chamber occupied by said annular suspension portion of said diaphragm has a rounded cup like shape, the curvature of said chamber side wall conforming substantially to the curvature that a radially outer portion of said U-cross section depressed annular suspension portion tends to take in response to an increase in pressure above the diaphragm tending to force same downward in the chamber, the top edge portion of the radially outer portion of the annular suspension portion depending from said rim and downward flush along a top portion of said side wall and diverging radially inward away from said side wall with the diaphragm in its normal, rest, raised position in the chamber, said diaphragm depressed portion radially outer portion being responsive to an increase in pressure above said diaphragm to unroll progressively downward close along the concavely curved side wall of said chamber to a lower operating position in the chamber and with a downwardly opening, narrow angular squish area advancing downward between the side wall of the chamber and the radially outer portion of the U-shaped annular suspension portion brought together by an increase in pressure above the diaphragm, the curvature of said chamber side wall corresponding substantially to the curvature that the diaphragm naturally assumes in response to increasing pressure above it in the chamber, such that the curved side wall of the chamber supports the radially outer portion of the U-shaped annular suspension portion of the diaphragm as it unrolls downward therealong, so as to avoid stretching of the diaphragm material or trapped air pockets between the curved side wall of the chamber and the radially outer portion of the diaphragm.

7. The apparatus of claim 1 in which said central opening in said chamber bottom wall is tapered, being narrower at its inboard end, said transducer having a projection which is tapered at a lesser angle than said central opening, the minimum diameter of said projection being slightly less than that of said central opening and related thereto such that the projection is freely insertable up into said central opening with adequate space therebetween for air escape from the portion of said chamber beneath said diaphragm until said projection is nearly fully inserted into said central opening, whereat a slight further axial insertion causes said projection to block said central opening in an air tight manner, whereby preloading of the bottom of the diaphragm, due to insertion of said projection into said central opening is minimized.

8. A tissue pressure measuring and monitoring system as recited in claim 1 in which said side wall of said chamber is curved into the bottom wall thereof in a concave manner conforming substantially to the shape of the radially outer wall of said U-shaped depressed portion of said diaphragm when the latter is subjected to increased liquid pressure in the top portion of said chamber, said diaphragm having a depressed lower position within said chamber corresponding to a maximum usable pressure reading for liquid in said chamber above said diaphragm, in which lower position the air volume in the chamber below the diaphragm is minimized and very substantially less than the liquid volume in said chamber above said diaphragm, such that the pressure of liquid above said diaphragm is transferred through a minimum volume of air to said pressure transducer in said central opening.

9. A tissue measuring and monitoring system as recited in claim 1 including a tubular valve housing having one end fixedly extending from said pressure chamber member in coaxial relation with the aligned legs of said connecting passages, said syringe being releasably connected to a remote end of said tubular valve housing, means defining an automatic one way valve in said tubular valve housing for permitting fluid flow from the syringe to and through said interior chamber and through said tissue penetrating means but automatically preventing back flow of any fluid from said interior chamber to said syringe.

10. Apparatus for measuring fluid pressures and fluctuations thereof in tissues, comprising:
a pressure receiving device and a separate pressure measuring device;
said pressure receiving device comprising a member defining a pressure chamber having a top wall, side wall and a bottom wall, said bottom wall having an opening therein;
a pressure responsive flexible diaphragm within said chamber and dividing said chamber into separate liquid and air subchambers;
means for connecting said liquid subchamber to tissues in which fluid pressure is to be measured;
means to purge said liquid subchamber of said pressure receiving device with air and fill it with liquid;
said pressure measuring device comprising a pressure transducer having a protrusion insertable in said opening in said bottom wall, said opening in said bottom wall opening to said air subchamber, such that said protrusion is shielded from liquid contact by said diaphragm but as applied thereto the pressure of liquid in said liquid subchamber through action of the diaphragm and correspondingly pressurizing the air in said air subchamber, said measuring device including a housing having a support surface on which to lay said purge means, said pressure transducer being located on said housing adjacent said support surface, said transducer projection being sealingly received in said opening in said bottom wall of said chamber member with said purge means laid on said support surface of said housing, a cover fitted to said housing and adapted to close over said member defining said pressure chamber in a manner to hold same fixedly on said housing and with respect to said projection, said housing and cover together defining a closed surround containing said pressure chamber defining member, said closed surround having opposed openings through which snugly project said purge means and said means for connecting said liquid subchamber to tissue, said pressure chamber defining member, purge means and means connecting said liquid subchamber to tissue being as a unit implacable in and removable from said enclosed relation by said housing and cover and being operable to inject liquid into tissue while so enclosed, said housing having a pressure read out means exposed outside said cover for reading out the pressure in said chamber and located adjacent said support surface.

11. The apparatus of claim 10 in which said opening in said bottom wall is tapered toward said air subchamber, said projection being tapered at a lesser angle toward the end thereof and insertable in said opening, the minimum diameters of said opening and projection being related such that air is free to flow out of said air subchamber through said opening during insertion of said projection into said opening and until said projection is substantially fully inserted in said opening whereupon only a very small fractional further increment of insertion of said projection into said opening is required to effect sealing between the minimum diameter end of said projection and the minimum diameter end of said opening.

12. Apparatus for measuring fluid pressures and fluctuations thereof in tissues, comprising:
a member defining a pressure chamber having a top wall, side wall and a bottom wall, said bottom wall having an opening therein for measuring of the pressure in said chamber;
a pressure responsive flexible diaphragm within said chamber and dividing said chamber into separate liquid and air subchambers, said diaphragm having a depressed annular suspension portion of U-cross section depending from an annular rim and a central head;
means for connecting said liquid subchamber to tissues in which fluid pressure is to be measured;
means to purge said liquid subchamber of air and fill it with liquid;
the side wall of said chamber being concavely curved downward and then radially inward to meet the bottom wall of said chamber, so that the portion of said chamber occupied by said annular suspension portion of said diaphragm has a rounded cup like shape, the curvature of said chamber side wall conforming substantially to the curvature that a radially outer portion of said U-cross section depressed annular suspension portion tends to take in response to an increase in pressure above the diaphragm tending to force same downward in the chamber, the top edge portion of the radially outer portion of the annular suspension portion depending from said rim and downward flush along a top portion of said side wall and diverging radially inward away from said side wall with the diaphragm in its normal, rest, raised position in the chamber, said diaphragm depressed portion radially outer portion being responsive to an increase in pressure above said diaphragm to unroll progressively downward close along the concavely curved side wall of said chamber to a lower operating position in the chamber and with a downwardly opening, narrow angular squish area advancing downward between the side wall of the chamber and the radially outer portion of the U-shaped annular suspension portion brought together by an increase in pressure above the diaphragm, the curvature of said chamber side wall corresponding substantially to the curvature that the diaphragm naturally assumes in response to increasing pressure above it in the chamber, such that the curved side wall of the chamber supports the radially outer portion of the U-shaped annular suspension portion of the diaphragm as it unrolls downward therealong, so as to avoid stretching of the diaphragm material or trapped air pockets between the curved side wall of the chamber and the radially outer portion of the diaphragm.

13. A disposable device for use in measuring fluid pressures and changes thereof in tissues, comprising:
a pressure chamber member defining a pressure chamber;
a pressure sensitive diaphragm disposed in said chamber and dividing it into liquid and air subchambers;
insertion means freely openly connected to said liquid subchamber and arranged for insertion into said tissues;
a syringe connected to said liquid subchamber and having plunger means for advancing liquid from said syringe through said liquid subchamber and insertion means to said tissues; and
automatic means interposed between said syringe and said liquid subchamber and automatically responsive to pressure drops thereacross for (1) automatically permitting liquid to flow freely from said syringe through said pressure chamber to said insertion means but (2) automatically preventing escape of pressure from said pressure chamber and insertion means by pushing back said plunger means in said syringe and (3) automatically preventing contamination of said syringe by blocking back flow of liquid into said syringe from said insertion means and tissue, said automatic means including a tubular valve housing extending from said syringe to said pressure chamber member, said automatic means also including an automatic one way valve member shiftable in said tubular valve housing for permitting free liquid flow from the syringe to and through said liquid subchamber and through said insertion means but automatically preventing back flow of any fluid from said liquid subchamber to said syringe.

14. A disposable device for use in measuring fluid pressures and changes thereof in tissues, comprising:
- a syringe and a plunger therein;
- a pressure chamber member defining a pressure chamber having top, bottom, and side walls;
- a pressure sensitive diaphragm disposed in said chamber and dividing it into upper liquid and lower air subchambers; and
- insertion means for insertion into said tissues, said device being substantially T-shaped with said pressure chamber member at the base of the T and said syringe and at least an adjacent portion of said insertion means as arms of the T, said top wall having passages comprising coaxial lateral blind legs entering from opposite sides thereof and having adjacent blind ends spaced by a central portion of said top wall, said lateral legs communicating with coaxial passages in said syringe and insertion means, said diaphragm being of reentrant type having a rim recessed in the side walls of said pressure chamber at said top wall, said diaphragm having a flexible wall depending in a flush manner from said rim down from said top wall and close along said side walls of the air subchamber, said top wall passages having respective depending legs opening down into said liquid subchamber substantially flush with adjacent portions of said rim and diaphragm flexible wall to avoid entrapment of air in said liquid subchamber when the device is positioned with the insertion means uppermost and the syringe is actuated to drive liquid through said liquid subchamber and insertion means.

* * * * *

UNITED STATES PATENT AND TRADEMARK OFFICE
CERTIFICATE OF CORRECTION

PATENT NO. : 4,817,629

DATED : April 4, 1989

INVENTOR(S) : Scott J. DAVIS, Wayne N. WARFIELD, William M. BOOTH, III

It is certified that error appears in the above-identified patent and that said Letters Patent is hereby corrected as shown below:

Col. 8, line 11; change "wall, said wall" to ---wall, side wall---.

Signed and Sealed this

Twenty-third Day of January, 1990

*Attest:*

JEFFREY M. SAMUELS

*Attesting Officer*     *Acting Commissioner of Patents and Trademarks*